US012741917B2

(12) United States Patent
Cho et al.

(10) Patent No.: US 12,741,917 B2
(45) Date of Patent: Sep. 22, 2026

(54) METHOD FOR MANUFACTURING ALPHA-METHYLSTYRENE

(71) Applicant: LG CHEM, LTD., Seoul (KR)

(72) Inventors: Jangkeun Cho, Daejeon (KR); Jooyoung Cheon, Daejeon (KR); Daeheung Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 197 days.

(21) Appl. No.: 18/717,940

(22) PCT Filed: Sep. 21, 2023

(86) PCT No.: PCT/KR2023/014341
§ 371 (c)(1),
(2) Date: Jun. 7, 2024

(87) PCT Pub. No.: WO2024/101650
PCT Pub. Date: May 16, 2024

(65) Prior Publication Data

US 2024/0417349 A1 Dec. 19, 2024

(30) Foreign Application Priority Data

Nov. 11, 2022 (KR) ........................ 10-2022-0150229

(51) Int. Cl.
*C07C 15/46* (2006.01)
*C07C 5/32* (2006.01)

(52) U.S. Cl.
CPC .............. *C07C 15/46* (2013.01); *C07C 5/324* (2013.01)

(58) Field of Classification Search
CPC .......... B01J 23/75; B01J 23/755; B01J 27/24; C07C 5/333; C07C 15/46; C07C 5/321; C07C 5/324; C07C 15/44; C07C 2521/04; C07C 2527/24
See application file for complete search history.

(56) References Cited

U.S. PATENT DOCUMENTS

| | | | |
|---|---|---|---|
| 4,590,324 | A | 5/1986 | Satek |
| 5,530,166 | A | 6/1996 | Zakoshansky et al. |
| 2011/0213189 | A1 | 9/2011 | Mishima et al. |
| 2013/0237736 | A1 | 9/2013 | Keenan |
| 2018/0273445 | A1 | 9/2018 | Kim et al. |

FOREIGN PATENT DOCUMENTS

| | | | |
|---|---|---|---|
| CN | 104437467 | B | 5/2017 |
| CN | 114425388 | A | 5/2022 |
| CN | 114426547 | A | 5/2022 |
| JP | 2001-500137 | A | 1/2001 |
| JP | 2003-517027 | A | 5/2003 |
| KR | 1993-0003460 | B1 | 4/1993 |
| KR | 10-0367444 | B1 | 5/2003 |
| KR | 2014-0133844 | A | 11/2014 |
| KR | 10-1501318 | B1 | 3/2015 |
| KR | 10-1520381 | B1 | 5/2015 |
| KR | 20170074745 | A | 6/2017 |
| KR | 10-1997814 | B1 | 7/2019 |
| WO | 2001-044146 | A1 | 6/2001 |

OTHER PUBLICATIONS

Fedotov, A. S. et al., "Dehydrogenation of cumene to α-methylstyrene on [Re,W]/y—Al2O3(K,Ce)/α—Al2O3 and [Fe, Cr]/y—Al2O3(K,Ce)/α—Al2O3 porous ceramic catalytic converters", Petroleum Chemistry (2020), vol. 60, No. 11, pp. 1268-1283.
Madhavi, J. et al. "N2 as a co-soft oxidant along with CO2 in ethylbenzene dehydrogenation to styrene over y-Al2O3 supported Co—Mo nitride catalysts" Journal of CO2 Utilization (2014), vol. 8, pp. 21-26.
Gurram, V. R. et al., "Synthesis and industrial catalytic applications of binary and ternary molybdenum nitrides: a review", Catalysis Surveys from Asia (2018), vol. 22, pp. 166-180.

*Primary Examiner* — Vishal V Vasisth
(74) *Attorney, Agent, or Firm* — BRYAN CAVE LEIGHTON PAISNER LLP

(57) ABSTRACT

A method for manufacturing alpha-methylstyrene includes dehydrogenating cumene in a reactor under a catalyst to manufacture alpha-methylstyrene, wherein one or more of nitrogen ($N_2$) and carbon dioxide ($CO_2$) are added during the dehydrogenation reaction of cumene, and wherein the catalyst comprises a carrier, and a metal nitride-based catalyst component supported on the carrier.

7 Claims, No Drawings

METHOD FOR MANUFACTURING ALPHA-METHYLSTYRENE

REFERENCE TO RELATED APPLICATIONS

The present application is a National Phase entry pursuant to 35 U.S.C. § 371 of International Application No, PCT/KR2023/014341 filed Sep. 21, 2023, and claims priority to and the benefit of Korean Patent Application No. 10-2022-0150229 filed in the Korean Intellectual Property Office on Nov. 11, 2022, the entire contents of which are incorporated herein by reference.

TECHNICAL FIELD

The present application relates to a method for manufacturing alpha-methylstyrene.

BACKGROUND ART

Alpha-methylstyrene (AMS) is diversely used as an additive when manufacturing specific copolymers such as ABS (acrylonitrile butadiene styrene copolymer), and novel polymers.

Alpha-methylstyrene is produced as a by-product of a phenol manufacturing process. Phenol and alpha-methylstyrene are generally manufactured through oxidation and cleavage processes, and the like, using cumene as a raw material. More specifically, conventionally alpha-methylstyrene is manufactured as a by-product of a cleavage reaction of cumene peroxide under an acid catalyst. This is, dimethylbenzyl alcohol (DMBA) contained in the cumene peroxide reactant is converted to alpha-methylstyrene and water.

However, a method for manufacturing alpha-methylstyrene of the related art has problems in that, since alpha-methylstyrene is produced as a by-product of a phenol manufacturing process, the amount produced is small and yield of the produced alpha-methylstyrene is also only about 70% to 80%.

Accordingly, studies on a method for manufacturing alpha-methylstyrene capable of increasing the yield of the manufactured alpha-methylstyrene have been required in the art.

SUMMARY OF THE INVENTION

The present application has been made in an effort to provide a method for manufacturing alpha-methylstyrene.

An exemplary embodiment of the present application provides a method for manufacturing alpha-methylstyrene, the method comprising: dehydrogenating cumene in a reactor under a catalyst to manufacture alpha-methylstyrene, wherein one or more of nitrogen ($N_2$) and carbon dioxide ($CO_2$) are added during the dehydrogenation reaction of cumene, and wherein the catalyst comprises a carrier; and a metal nitride-based catalyst component supported on the carrier.

The method for manufacturing alpha-methylstyrene according to an exemplary embodiment of the present application directly dehydrogenates cumene to manufacture alpha-methylstyrene, whereby it is not necessary to proceed with the oxidation and cleavage processes of the related art, thereby reducing process costs, process risks, and providing eco-friendly characteristics. In addition, since carbon dioxide can be used as a reactant, there is an advantage in that the amount of carbon dioxide emissions can be reduced.

The method for manufacturing alpha-methylstyrene according to an exemplary embodiment of the present application is excellent in terms of the conversion ratio of cumene and the selectivity of alpha-methylstyrene to be produced.

DETAILED DESCRIPTION

Hereinafter, the present application will be described in more detail.

Throughout the present specification, when a member is referred to as being "on" another member, the member can be in direct contact with another member or an intervening member may also be present.

In the present specification, when a part is referred to as "comprising" a certain component, it means that the part can further comprise another component, not excluding another component, unless explicitly described to the contrary.

Alpha-methylstyrene (AMS) is an additive for improving the heat resistance of acrylonitrile butadiene styrene copolymer (ABS), and its demand is increasing by 4% to 5% every year as sales of ABS heat-resistant products increase.

As described above, in the related art, alpha-methylstyrene has been manufactured as a by-product of a phenol manufacturing process by manufacturing phenol and alpha-methylstyrene through oxidation and cleavage processes, and the like, using cumene as a raw material. More specifically, in the related art, cumene, a starting material, is oxidized to manufacture a mixture of cumene peroxide and cumyl alcohol, and the mixture of cumene peroxide and cumyl alcohol is subjected to a cleavage reaction to manufacture phenol and acetone from the cumene peroxide, and manufacture alpha-methylstyrene from the cumyl alcohol. However, such a technology of the related art is mainly aimed at manufacturing phenol from cumene, and since the alpha-methylstyrene is manufactured as a by-product of a phenol manufacturing process, there is a problem in that the amount of alpha-methylstyrene produced is small, so the supply of alpha-methylstyrene is low compared to the demand. When the amount of alpha-methylstyrene produced is increased in the process of the related art in order to meet the amount of alpha-methylstyrene demanded, the amounts of phenol and acetone produced decrease due to a trade-off relationship, so the need to develop a new process is emerging.

Accordingly, the present application is intended to provide a method for manufacturing alpha-methylstyrene by directly dehydrogenating cumene, which can replace the manufacturing process of alpha-methylstyrene of the related art.

A method for manufacturing alpha-methylstyrene according to an exemplary embodiment of the present application comprises dehydrogenating cumene in a reactor under a catalyst to manufacture alpha-methylstyrene, wherein one or more of nitrogen ($N_2$) and carbon dioxide ($CO_2$) are added during the dehydrogenation reaction of cumene.

In an exemplary embodiment of the present application, the dehydrogenation reaction of cumene may be represented by Reaction Scheme 1 below. In particular, during the dehydrogenation reaction of cumene, one or more of nitrogen ($N_2$) and carbon dioxide ($CO_2$) are added.

[Reaction Scheme 1]

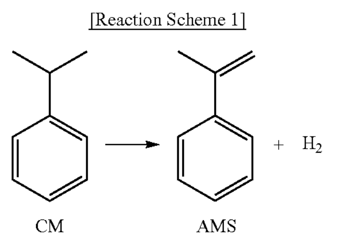

CM AMS

In the related art, steam was used in order to improve stability of the reaction and the like in the process of directly dehydrogenating cumene to produce alpha-methylstyrene. However, in the dehydrogenation reaction of cumene using steam, there are problems in that the conversion ratio of cumene as a reactant is low, or the selectivity of alpha-methylstyrene as a reaction product is low, making it difficult to use commercially and increasing the process operating cost.

However, according to the method for manufacturing alpha-methylstyrene according to an exemplary embodiment of the present application, steam is not applied, unlike the related art, and one or more of nitrogen ($N_2$) and carbon dioxide ($CO_2$) are added during the dehydrogenation reaction of cumene, so that it is possible to improve not only the stability of the reaction but also the conversion ratio of cumene and the selectivity of alpha-methylstyrene at the same time. In addition, in the dehydrogenation reaction of cumene using steam of the related art, the process operating cost was excessively high. By contrast, in an exemplary embodiment of the present application, one or more of nitrogen ($N_2$) and carbon dioxide ($CO_2$) are applied instead of steam, so that energy can be reduced by approximately 10 times or more based on 1 ton of a reaction product, and thus the process operating cost can be significantly reduced.

The dehydrogenation reaction of cumene can be performed at temperatures ranging from 500° C. to 650° C. or at temperatures ranging from 550° C. to 600° C. Additionally, the dehydrogenation reaction of cumene may be performed at normal pressure.

In an exemplary embodiment of the present application, nitrogen alone may be added during the dehydrogenation reaction of cumene. In addition, in an exemplary embodiment of the present application, carbon dioxide alone may be added during the dehydrogenation reaction of cumene.

Additionally, in an exemplary embodiment of the present application, nitrogen and carbon dioxide may both be added during the dehydrogenation reaction of cumene. In this case, a volume ratio of nitrogen: carbon dioxide added may be 1:9 to 9:1 or 2:8 to 8:2.

When nitrogen and carbon dioxide are added simultaneously during the dehydrogenation reaction of cumene, nitrogen and carbon dioxide may be added through separate lines, respectively, or nitrogen and carbon dioxide may be mixed to satisfy the above-mentioned volume ratio and then added through one line.

In an exemplary embodiment of the present application, the catalyst is a catalyst for the dehydrogenation reaction of cumene, and the catalyst comprises a carrier; and a metal nitride-based catalyst component supported on the carrier. More specifically, the catalyst component may comprise $Mo_2N$. The catalyst component comprising $Mo_2N$ may be composed of $Mo_2N$, and may additionally comprise one or more of Co and Ni, in addition to $Mo_2N$.

The carrier may be selected from alumina, silica, clay, carbon, zirconia, titania, mesoporous molecular sieve, and mixtures thereof, but is not limited thereto. More preferably, the carrier is alumina.

In an exemplary embodiment of the present application, when the catalyst comprises a metal nitride-based catalyst component and nitrogen ($N_2$) is added during the dehydrogenation reaction of cumene, the added nitrogen ($N_2$) can be converted to ammonia by N in a lattice of the metal nitride-based catalyst component and adsorbed on the carrier, whereby the stability and reactivity of the catalyst can be increased. In addition, in an exemplary embodiment of the present application, when the catalyst comprises a metal nitride-based catalyst component and carbon dioxide ($CO_2$) is added during the dehydrogenation reaction of cumene, reverse-water gas shift reactivity of carbon dioxide can be exhibited due to the metal nitride-based catalyst component, so the yield of alpha-methylstyrene can be increased for reaction equilibrium.

Therefore, if the catalyst does not comprise a metal nitride-based catalyst component such as $Mo_2N$, it is difficult to expect high reactivity even when one or more of nitrogen ($N_2$) and carbon dioxide ($CO_2$) are added during the dehydrogenation reaction of cumene. In particular, when using steam in the conventional process of directly dehydrogenating cumene to produce alpha-methylstyrene, metal alone was applied as a catalyst. Therefore, in the conventional process for producing alpha-methylstyrene using steam, if only the catalyst is changed to a metal nitride-based catalyst or if steam is changed to nitrogen ($N_2$) and/or carbon dioxide ($CO_2$) under a catalyst of metal alone, the same effect as an exemplary embodiment of the present application cannot be achieved.

The method for manufacturing alpha-methylstyrene according to an exemplary embodiment of the present application directly dehydrogenates cumene to manufacture alpha-methylstyrene, whereby it is not necessary to proceed with the oxidation and cleavage processes of the related art, thereby reducing process costs and process risks and providing eco-friendly characteristics. In addition, since carbon dioxide can be used as a reactant, there is an advantage in that an amount of emission of carbon dioxide can be reduced.

The method for manufacturing alpha-methylstyrene according to an exemplary embodiment of the present application is excellent in terms of the conversion ratio of cumene and the selectivity of alpha-methylstyrene to be produced.

Below, Examples will be described in detail for specifically describing the present application. However, the Examples according to the present application may be modified in other forms, and the scope of the present application is not construed as being limited to the Examples described in detail below. The Examples of the present application are provided to more completely explain the present application to one skilled in the art.

EXAMPLES

Example 1

$(CH_2)_6N_4$ (hexamethylenetetramine) as a N source was supported on $\gamma$-$Al_2O_3$ through incipient wetness impregnation, which was then sufficiently dried in a convection oven at 100° C. Thereafter, $(NH_4)_6Mo_7O_{24}\cdot 4H_2O$ as a Mo precursor was supported in the same way, which was then sufficiently dried in a convection oven at 100° C. In this case, a supported amount of Mo was set to 10 wt % based on $\gamma$-$Al_2O_3$, and $(NH_4)_6Mo_7O_{24}\cdot 4H_2O$ and $(CH_2)_6N_4$ was set to 1:15 in a molar ratio.

After the support of catalyst was completed, 2 g of the sample was loaded into a fixed bed reactor and heat-treated for 4 hours under conditions of 600° C. and $N_2$ to change the catalyst to the form of to $Mo_2N/\gamma$-$Al_2O_3$. Then, the temperatures of lines entering the reactor from a pump were set to 160° C. higher than the boiling point of cumene, and the temperature of a trap at a rear end of the reactor was set to 0° C.

After the catalyst pretreatment and the reactor setting were completed in this way, cumene was added at a flow rate of 0.066 ml/min through the pump, and at the same time, nitrogen ($N_2$) was added into the gas line at a flow rate of 120 ml/min to proceed with the reaction, thereby producing alpha-methylstyrene.

Example 2

The same process as in Example 1 was performed, except that, instead of adding nitrogen alone, nitrogen ($N_2$) and carbon dioxide ($CO_2$) were mixed at a volume ratio of 8:2 ($N_2$:$CO_2$) and then added.

Example 3

The same process as in Example 1 was performed, except that, instead of adding nitrogen alone, nitrogen ($N_2$) and carbon dioxide ($CO_2$) were mixed at a volume ratio of 5:5 ($N_2$:$CO_2$) and then added.

Example 4

The same process as in Example 1 was performed, except that, instead of adding nitrogen alone, nitrogen ($N_2$) and carbon dioxide ($CO_2$) were mixed at a volume ratio of 2:8 ($N_2$:$CO_2$) and then added.

Example 5

The same process as in Example 1 was performed, except that, instead of adding nitrogen alone, carbon dioxide ($CO_2$) alone was added.

Comparative Example 1

The same process as in Example 1 was performed, except that Re, $W/Al_2O_3$ was applied as a catalyst, instead of $Mo_2N/\gamma$-$Al_2O_3$, and steam was added instead of nitrogen.

Comparative Example 2

The same process as in Example 1 was performed, except that Fe, $Cr/Al_2O_3$ was applied as a catalyst, instead of $Mo_2N/\gamma$-$Al_2O_3$, and steam was added instead of nitrogen.

Comparative Example 3

The same process as in Example 1 was performed, except that steam was added instead of nitrogen.

Comparative Example 4

The same process as in Example 3 was performed, except that Fe—Cr oxide/$Al_2O_3$ was applied as a catalyst, instead of $Mo_2N/\gamma$-$A_2O_3$.

Experimental Example 1

The reaction products comprising alpha-methylstyrene prepared in the Examples and the Comparative Examples were analyzed and shown in Table 1 below. Analysis of the reaction product comprising alpha-methylstyrene was performed using gas chromatography (GC) equipped with an HP-1 column.

1) Column: HP-1 (L: 30 m, ID: 0.32 mm, film: 1.05 m)
2) Injection volume: 1 μℓ
3) Inlet Temp.: 250° C., Pressure: 6.92 psi, Total flow: 64.2 ml/min, Split flow: 60 ml/min, spilt ratio: 50:1
4) Column flow: 1.2 ml/min
5) Oven temp.: 100° C./5 min-15° C./min-250° C./5 min
6) Detector temp.: 280° C., H2: 35 ml/min, Air: 300 ml/min, He: 20 ml/min
7) GC Model: Agilent 7890

In the present application, the "conversion ratio (%)" refers to a ratio of a reactant converting to a product, and for example, the conversion ratio of cumene may be defined by the following equation.

$$\text{Conversion ratio (\%)} = [(\text{number of moles of reacted cumene})/(\text{number of moles of supplied cumene})] \times 100$$

In the present application, the "selectivity (%)" is defined as a value obtained by dividing the amount of change in alpha-methylstyrene by the amount of change in cumene. For example, the selectivity may be represented by the following equation.

$$\text{Selectivity (\%)} = [((\text{number of moles of produced alpha-methylstyrene})/(\text{number of moles reacted cumene})] \times 100$$

In the present application, the "yield (%)" is defined as a value obtained by dividing the number of moles of alpha-methylstyrene, a product, by the number of moles of cumene, a raw material. For example, the yield can be represented by the following equation.

$$\text{Yield (\%)} = [(\text{number of moles of produced alpha-methylstyrene})/(\text{number of moles of supplied cumene})] \times 100$$

TABLE 1

| | Conversion rate of cumene (%) | Selectivity of alpha-methylstyrene (%) | Yield of alpha-methylstyrene (%) |
|---|---|---|---|
| Example 1 | 56.9 | 91.1 | 51.8 |
| Example 2 | 60.1 | 91.2 | 54.8 |
| Example 3 | 59 | 92.1 | 54.3 |
| Example 4 | 69.8 | 94.6 | 66.0 |
| Example 5 | 62.2 | 95.6 | 59.4 |
| Comparative Example 1 | 70 | 72 | 50.4 |
| Comparative Example 2 | 28 | 90 | 25.2 |
| Comparative Example 3 | 99 | 0 | 0 |

TABLE 1-continued

| | Conversion rate of cumene (%) | Selectivity of alpha-methylstyrene (%) | Yield of alpha-methylstyrene (%) |
|---|---|---|---|
| Comparative Example 4 | 62.2 | 23 | 14.3 |

As shown in the above results, it can be confirmed that in the dehydrogenation reaction of cumene using steam as in Comparative Examples 1 and 2, the conversion ratio of cumene, a reactant, was low or the selectivity of alpha-methylstyrene, a reaction product, was low.

In addition, when a metal nitride-based catalyst and steam were applied during the dehydrogenation reaction of cumene as in Comparative Example 3, alpha-methylstyrene could not be produced because the metal nitride-based catalyst was damaged by steam.

In addition, it can be confirmed that when a metal catalyst other than a metal nitride-based catalyst and nitrogen/carbon dioxide were applied during the dehydrogenation reaction of cumene as in Comparative Example 4, the selectivity of alpha-methylstyrene was very low.

However, as in Examples 1 to 5, according to the method for manufacturing alpha-methylstyrene according to an exemplary embodiment of the present application, steam is not applied, unlike the related art, and one or more of nitrogen ($N_2$) and carbon dioxide ($CO_2$) are added during the dehydrogenation reaction of cumene, so that it is possible to improve not only the stability of the reaction but also the conversion ratio of cumene and the selectivity of alpha-methylstyrene at the same time.

Therefore, the method for manufacturing alpha-methylstyrene according to an exemplary embodiment of the present application directly dehydrogenates cumene to manufacture alpha-methylstyrene, whereby it is not necessary to proceed with the oxidation and cleavage processes of the related art, thereby reducing process costs and process risks and providing eco-friendly characteristics. In addition, since carbon dioxide can be used as a reactant, there is an advantage in that an amount of carbon dioxide emissions can be reduced.

The invention claimed is:

1. A method for manufacturing alpha-methylstyrene, the method comprising:

dehydrogenating cumene in a reactor under a catalyst to manufacture alpha-methylstyrene, wherein one or more of nitrogen ($N_2$) and carbon dioxide ($CO_2$) are added during the dehydrogenation reaction of cumene, wherein the catalyst comprises a carrier; and a metal nitride-based catalyst component supported on the carrier, and wherein the metal nitride-based catalyst component comprises $Mo_2N$.

2. The method of claim 1, wherein nitrogen or carbon dioxide alone is added during the dehydrogenation reaction of cumene.

3. The method of claim 1, wherein nitrogen and carbon dioxide are both added during the dehydrogenation reaction of cumene, and wherein a volume ratio of nitrogen: carbon dioxide added is 1:9 to 9:1.

4. The method of claim 3, wherein the volume ratio of nitrogen:carbon dioxide added is 2:8 to 8:2.

5. The method of claim 1, wherein the metal nitride-based catalyst component further comprises one or more of Co and Ni.

6. The method of claim 1, wherein the carrier is selected from alumina, silica, clay, carbon, zirconia, titania, mesoporous molecular sieve, and mixtures thereof.

7. The method of claim 1, wherein the dehydrogenation reaction of cumene is performed at a temperature ranging from 500° C. to 650° C.

* * * * *